United States Patent [19]

Fukuda et al.

[11] 4,416,820
[45] Nov. 22, 1983

[54] INDOLE DERIVATIVES AND A METHOD FOR PRODUCTION OF PEPTIDES

[75] Inventors: Tsunehiko Fukuda, Minoo; Shigeru Kobayashi, Neyagawa; Masahiko Fujino, Takarazuka, all of Japan

[73] Assignee: Takeda Chemical Industries, Ltd., Osaka, Japan

[21] Appl. No.: 339,054

[22] Filed: Jan. 13, 1982

[30] Foreign Application Priority Data

Jan. 14, 1981 [JP]  Japan ................................. 56-4506

[51] Int. Cl.³ .................. C07C 103/52; C07D 209/04
[52] U.S. Cl. .............................. 548/496; 260/112.5 R
[58] Field of Search ...................... 424/177; 260/112.5, 260/326.12 A, 326.12 R; 548/469

[56] References Cited

U.S. PATENT DOCUMENTS 3,845,097 10/1974 Toyoshima et al. ................ 549/339
3,919,291 11/1975 Toyoshima et al. ................ 560/159
3,997,516 12/1976 Nishimura .................... 260/112.5 R

FOREIGN PATENT DOCUMENTS 1351437 5/1974 United Kingdom .

OTHER PUBLICATIONS

*Chemical Abstracts,* 79, p. 42, (1973), Abstract No. 73770s.
*Chemical Abstracts,* 82, p. 32, (1975), Abstract No. 149373z.
Proceedings of the 18th Symposium on Peptide Chemistry, Nishinomiya, Nov. 15–16, 1980; Fujino et al., pp. 21–24.
Bulletin of the Chemical Society of Japan, vol. 45, 2852–2855, (1972), Ohno et al.
Journal of the Chemical Society, Perkin Transactions 1, pp. 627–631, (1977), Yakir S. Klausner et al.
Chemical & Pharmaceutical Bulletin, vol. 29, Oct. 1981, pp. 2825–2831.

*Primary Examiner*—Delbert R. Phillips
*Assistant Examiner*—F. T. Moezie
*Attorney, Agent, or Firm*—Wenderoth, Lind & Ponack

[57] ABSTRACT

An indole group in an amino acid or a peptide can be protected with a group shown by the formula:

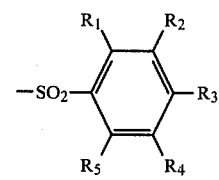

wherein $R_1$ and $R_5$ each is hydrogen, methyl or methoxy; $R_2$ and $R_4$ each is hydrogen or methyl; and $R_3$ is methyl or methoxy, and said group may easily be removed without affecting the amino acid or the peptide to be derived from the protected amino acid or peptide. Thus, the present invention is useful in the synthesis of a peptide containing an indole group.

9 Claims, No Drawings

INDOLE DERIVATIVES AND A METHOD FOR PRODUCTION OF PEPTIDES

This invention relates to indole derivatives and a method of producing peptides.

It is known that a number of undesirable side reactions tend to occur in the course of production of peptides containing indole group-containing amino acid residues. For example, N-acyltryptophan may form a carboline compound in trifluoroacetic acid. When such amino-protecting groups as t-butyloxycarbonyl, p-methoxybenzyloxycarbonyl, etc. are removed by treatment with trifluoroacetic acid, or O-nitrophenylsulfenyl is removed by treatment with hydrochloric acid, a fairly high proportion of indole groups are t-butylated, p-methoxybenzylated or O-nitrophenylsulfenylated as the case may be. Moreover, when a peptide condensation reaction is performed by the azide method, indole groups may be nitrosated in the case of tryptophan-containing peptides. In order to preclude side reactions in the elimination of amino-protecting groups by acid treatment, such additive agent as ethanedithiol or thioanisole is sometimes employed but such procedures have never completely overcome the difficulties. As an omnibus measure for preventing occurrence of these side reactions, attempts were made to protect indole groups with formyl or benzyloxycarbonyl. However, the former protective group requires treatment with a base for removal and the latter group requires a complicated operation for introduction. Therefore, these methods have not been generally practiced. Under the circumstances, the present inventors investigated various sulfonic acid type protective groups which could be easily introduced into indole groups, would not give rise to side reactions involving indole groups, would be sufficiently stable in the course of general peptide synthesis, and could be easily removed at a final stage of synthesis. The present invention is based on the results of the above research and investigation.

This invention is therefore directed to (1) an indole derivative, inclusive of salts thereof, which has the formula:

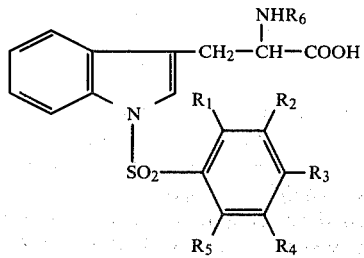

wherein $R_1$ and $R_5$ each is hydrogen, methyl or methoxy; $R_2$ and $R_4$ each is hydrogen or methyl; $R_3$ is methyl or methoxy; and $R_6$ is hydrogen or an α-amino-protecting group, and (2) a method of producing a peptide containing an indole group which comprises protecting the indole group of an indole group-containing starting compound with a substituted benzenesulfonyl group of the formula:

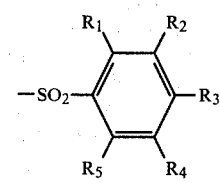

wherein $R_1$, $R_2$, $R_3$, $R_4$ and $R_5$ are as respectively defined hereinbefore, subjecting the protected compound to a peptide synthesis and then removing the protective group with an acid.

Referring to the general formulas (I) and (II), said substituted benzenesulfonyl group may for example be p-toluenesulfonyl, 2,4-dimethoxybenzenesulfonyl, p-methoxybenzenesulfonyl, 2,4,6-trimethoxybenzenesulfonyl, 4-methoxy-2,6-dimethylbenzenesulfonyl, pentamethylbenzenesulfonyl, 4-methoxy-2,3,5,6-tetramethylbenzenesulfonyl, 4-methoxy-2,3,6-trimethylbenzenesulfonyl or the like.

The indole derivative of formula (I) can be prepared by reacting a compound of formula (III):

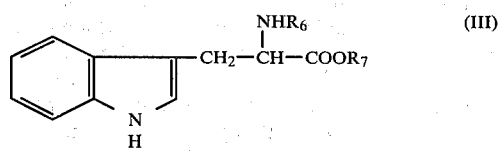

wherein $R_6$ is an α-amino-protecting group; and $R_7$ is a carboxy-protecting group,
with a compound of formula (IV):

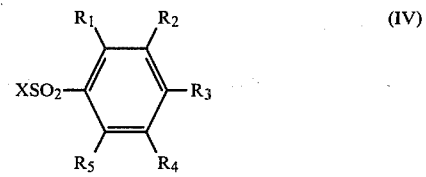

wherein X is halogen; and $R_1$, $R_2$, $R_3$, $R_4$ and $R_5$ are as respectively defined hereinbefore.

The compound (III) may be any of L-, D- and racemic compounds, and X in formula (IV) is preferably a chlorine atom. The above reaction is conducted in the presence of a base. The reaction may be carried out at a temperature within the range of, for example, about −10° C. to +50° C. and in a solvent such as dimethylformamide, dioxane, tetrahydrofuran, dichloromethane or the like. $R_6$ in formula (III) may be a known α-amino-protecting group such as t-butoxycarbonyl, carbobenzoxy, trityl, o-nitrophenylsulphenyl, 2-(p-biphenyl)-isopropoxycarbonyl or the like, and $R_7$ may be a known carboxy-protecting group such as benzyl, lower alkyl or the like. The base mentioned above may be one of those used commonly for the formation of a sulfonamide, such as sodium hydride, sodium hydroxide, etc. There are cases in which satisfactory results are obtained when the reaction is conducted in the presence of a phase transfer catalyst such as benzyltriethylammonium chloride, trioctylmethylammonium chloride, cetyltrimethylammonium chloride, etc.

The indole derivative (I) with thus protected amino, carboxy and indole groups can be modified, if desired, so that its protected amino group will be deprotected into a free amino group by a known procedure (e.g. catalytic reduction, treatment with trifluoroacetic acid) or/and its protected carboxy group deprotected into a free carboxy group by a known procedure (e.g. catalytic reduction, treatment with trifluoroacetic acid, alkali hydrolysis). The free carboxy group, in turn, may be activated by a known procedure (converted into e.g. acid anhydrides, azides, reactive esters).

The indole derivative (I) according to this invention corresponds to tryptophan with its indole group protected, and can be used with advantage in the production of tryptophan-containing peptides.

For said known procedures for protecting amino and carboxy groups, activating carboxy groups and synthesizing peptides, reference may be made, for example, to M. Bodansky and M. A. Ondetti, Peptide Synthesis, Interscience, New York, 1966; F. M. Finn and K. Hofmann, The Proteins, Vol. 2, H. Neurath, R. L. Hill (ed.), Academic Press Inc., New York, 1976; and N. Izumiya et al., "Peptide Gōsei," Maruzen K. K., 1975.

Then, after a peptide condensation reaction, the substituted benzenesulfonyl group of formula (II) is removed with an acid. This removal can be accomplished by a known acid treatment, e.g. with hydrogen fluoride, hydrogen bromide or methanesulfonic acid, or with trifluoroacetic acid in the presence of thioanisole or the like. When hydrogen fluoride is employed, the reaction conducted at $-20°$ C. to room temperature (most usually at $0°$ C.) for about one hour results in removal of the substituted benzenesulfonyl group from the indole group, along with removal of other protective groups present, to yield a free tryptophan-containing peptide. This reaction is preferably carried out in the presence of ethanedithiol, thioanisole, anisole or the like. When trifluoroacetic acid is employed as a deprotecting agent, the reaction is conducted in the presence of thioanisole, preferably at room temperature to $50°$ C. for about 2 hours.

The method according to this invention can be applied to the production of any indole group-containing peptide. As examples of such peptide may be mentioned such useful biologically active peptides as ACTH, alytensin, dynorphin, gastrin, bombesin, caerulein, calcitonin, glucagon, somatostatin, etc.

To protect the indole group of an indole group-containing compound with said substituted benzenesulfonyl group in the production of peptides according to this invention, the same procedure as that described for the introduction of the substituted by benzenesulfonyl group into the compound (III) can be employed. This procedure has the following advantageous features.

(1) The protective group represented by formula (II) can be removed by a simple treatment (e.g. with hydrogen fluoride) in a short time and in almost quantitative yield.

(2) The protective group (II) is so specific that it remains unaffected under the various conditions applied in the production of peptides such as the conditions necessary for removal of amino-protecting groups (e.g. treatment with trifluoroacetic acid, catalytic reduction) and conditions for removal of carboxy-protecting groups (e.g. treatment with trifluoroacetic acid, catalytic reduction, alkali hydrolysis).

(3) The protective group (II) can be used advantageously not only in the liquid-phase synthesis of tryptophan-containing peptides but also in the solid-phase synthesis thereof.

(4) With this protective group (II), said peptides can be produced in high purity and yield.

The following examples are further illustrative of this invention. It should be understood that, in this specification, amino acids, peptides, protective groups, reactive groups, etc. are sometimes referred to by the abbreviations according to IUPAC-IUB Commission on Biological Nomenclature or those used commonly in the relevant fields of science. Some of these abbreviations are given below.

Boc: t-butoxycarbonyl
Aoc: t-amyloxycarbonyl
Z: carbobenzoxy
Pms: p-tolylmethylsulfonyl
Tr: trityl
Tos: p-toluenesulfonyl
Tms: 2,4,6-trimethoxybenzenesulfonyl
Dmb: 2,4-dimethoxybenzenesulfonyl
Mbs: p-methoxybenzenesulfonyl
Mtr: 4-methoxy-2,3,6-trimethylbenzenesulfonyl
Mds: 4-methoxy-2,6-dimethylbenzenesulfonyl
HONb: N-hydroxy-5-norbornene-2,3-dicarboximide
ONb: HONb ester
OSu: N-hydroxysuccinimide ester
ONP: p-nitrophenyl ester
OBzl: benzylester
DCC: N,N'-dicyclohexylcarbodiimide
Lys: lysine
Gly: glycine
Glu: glutamic acid
Leu: leucine
Trp: tryptophan
Gln: glutamine
Asn: asparagine
Met: methionine
His: histidine
Arg: arginine
Val: valine
Ala: alanine
pGlu: pyroglutamic acid It should also be understood that where amino acids exist as optical isomer, the L-forms are meant unless otherwise specified.

EXAMPLE 1

In N,N-dimethylformamide (DMF) (10 ml) was dissolved Tr-Trp-OBzl (2.15 g, 4 mM), followed by addition of sodium hydride (50% in mineral oil, the same applies below; 240 mg, 5 mM) in a nitrogen gas stream. The reaction was conducted at room temperature for 20 minutes, after which p-toluenesulfonyl chloride (950 mg, 5 mM) was added. The reaction was further carried out at room temperature for 15 hours, at the end of which time ethyl acetate (50 ml) was added and the mixture was stirred for one hour. To the reaction mixture was added water (30 ml) with caution and the organic layer was taken and washed with 5% aqueous sodium hydrogen carbonate and water. After drying over sodium sulfate, the ethyl acetate was distilled off. The residue was purified by column chromatography on silica gel (15 g) using toluene as the solvent to give Tr-Trp(Tos)-OBzl. Yield 1.70 g (61.5%); m.p. $101°-103°$ C.; $[\alpha]_D^{24}+47.6°$ (c=0.5, DMF).

Elemental analysis: Calcd. for $C_{44}H_{39}N_2O_4S$: C, 76.54; H, 5.55; N, 4.06; S, 4.65; Found: C, 76.51; H, 5.55; N, 3.51; S, 4.67.

EXAMPLE 2

In 80% acetic acid (20 ml) was suspended Tr-Trp(Tos)-OBzl (1.3 g, 1.88 mM) and the mixture was stirred at room temperature for one hour, whereby the material was dissolved. The precipitated triphenylmethanol was filtered off and the filtrate was subjected to catalytic reduction for 4 hours in the presence of palladium black at room temperature. The catalyst was filtered off and the acetic acid was distilled off. The residue was recrystallized from water to give H-Trp(Tos)-OH. Yield 585 mg (86.9%); m.p. 227° C. (decomp.); $[\alpha]_D^{21} -29.2°$ (c=0.5, acetic acid).

Elemental analysis: Calcd. for $C_{18}H_{18}N_2O_4S.1/2-H_2O$: C, 58.83; H, 5.21; N, 7.63; S, 8.73; Found: C, 58.88; H, 5.23; N, 7.23; S, 8.72.

EXAMPLE 3

The procedure of Example 1 was repeated using Tr-Trp-OBzl (10.8 g, 20 mM), sodium hydride (1.44 g, 30 mM) and p-methoxybenzenesulfonyl chloride to give Tr-Trp(Mbs)-OBzl. Yield 14.2 g (100%); m.p. 94°–96° C.; $[\alpha]_D^{21} +43.1°$ (c=0.5, DMF).

Elemental analysis:

Calcd. for $C_{44}H_{39}N_2O_5S$: C, 74.71; H, 5.56; N, 3.96; S, 4.58; Found: C, 75.01; H, 5.35; N, 3.93; S, 4.50.

EXAMPLE 4

Tr-Trp(Mbs)-OBzl (14.2 g, 20 mM) was treated in the same manner as Example 2 to give H-Trp(Mbs)-OH. Yield 6.64 g (88.7%); m.p. 218°–220° C.; $[\alpha]_D^{24} -34.8°$ (c=0.5, acetic acid).

Elemental analysis: Calcd. for $C_{18}H_{18}N_2O_5S.1/2-H_2O$: C, 56.38; H, 5.00; N, 7.31; Found: C, 56.43; H, 4.92; N, 7.07.

EXAMPLE 5

In dichloromethane (10 ml) was dissolved Boc-Trp-OBzl (789 mg, 2 mM), followed by addition of cetyltrimethylammonium chloride (6.4 mg, 0.02 mM) and crushed sodium hydroxide (200 mg, 5 mM). Then, a solution of 2,4-dimethoxybenzenesulfonyl chloride (710 mg, 3 mM) in dichloromethane (3 ml) was added dropwise to the above mixture. The reaction was conducted at room temperature for 30 minutes, after which it was cooled and brought to pH 2 with 1 N—HCl. Following addition of water (10 ml), the solution was shaken and the dichloromethane layer was separated, washed with water and dried over sodium sulfate. The solvent was then distilled off to give Boc-Trp(Dmb)-OBzl. This product was dissolved in ethanol (10 ml), and under ice-cooling, a 1—N aqueous solution of sodium hydroxide (2.2 ml) was added. The reaction was continued at room temperature for one hour. The ethanol was distilled off and the residual aqueous solution was diluted with water (20 ml) and extracted with ether (20 ml). The water layer was cooled and brought to pH 3 with 10% aqueous citric acid. The solution was then extracted with ethyl acetate and the ethyl acetate layer was washed with water and dried over sodium sulfate. The solvent was then distilled off and the residue was treated with petroleum ether to give Boc-Trp(Dmb)-OH as a solid product. Yield 737 mg; (73%); m.p. 100° C. (decomp.); $[\alpha]_D^{22} -9.43°$ (c=0.5, DMF).

Elemental analysis: Calcd. for $C_{24}H_{28}N_2O_8S$: C, 57.13; H, 5.59; N, 5.55; S, 6.36; Found: C, 57.56; H, 5.86; N, 5.30; S, 6.28.

EXAMPLE 6

In the same manner as Example 5, Boc-Trp-OBzl (5.92 g, mM) and 2,4,6-trimethoxybenzenesulfonyl chloride (5.33 g, 20 mM) were reacted in dichloromethane (100 ml) in the presence of sodium hydroxide (1.5 g, 37.5 mM) and cetyltrimethylammonium chloride (49 mg, 0.15 mM). The reaction product was then hydrolyzed with an aqueous solution of sodium hydroxide to give Boc-Trp(Tms)-OH. Yield 7.32 g (91.2%); m.p. 82°–84° C.; $[\alpha]_D^{26} -15.4°$ (c=0.5, DMF).

Elemental analysis: Calcd. for $C_{25}H_{30}O_9N_2S$: C, 56.17; H, 5.66; N, 5.24; S, 6.00; Found: C, 56.37; H, 5.85; N, 4.91; S, 6.07.

EXAMPLE 7

In the same manner as Example 5, Boc-Trp-OBzl (789 mg, 2 mM) and 4-methoxy-2,6-dimethylbenzenesulfonyl chloride (702 mg, 3 mM) were reacted in dichloromethane in the presence of sodium hydroxide (200 mg) and cetyltrimethylammonium chloride (6.4 mg, 0.02 mM). The reaction product was then hydrolyzed with an aqueous solution of sodium hydroxide to give Boc-Trp(Mds)-OH. Yield 580 mg (57.8%); m.p. 78°–80° C.; $[\alpha]_D^{26} -21.2°$ (c=0.5, DMF).

Elemental analysis:

Calcd. for $C_{25}H_{30}O_7N_2S$: C, 59.74; H, 6.02; N, 5.58 S, 6.38; Found: C, 59.83; H, 6.17; N, 5.16 S, 6.08.

TEST EXAMPLE 1

The protected tryptophan samples (0.1 mM per sample) were each treated with hydrogen fluoride (1 ml) in the presence of ethanedithiol (0.5 ml) and anisole (0.1 ml) at 0° C. for one hour. The hydrogen fluoride was distilled off and the residue was dissolved in acetic acid (15 ml). The acetic acid was distilled off, the residue was dissolved in water (20 ml), and the insolubles were filtered off. The filtrate was extracted with ether. The water layer was diluted to 50 ml and subjected to amino acid analysis for estimating the yield of tryptophan. The results are set forth in Table 1.

TABLE 1

| Compound | Yield of Trp (%) |
| --- | --- |
| H—Trp(Tos)—OH | 19.0 |
| H—Trp(Mbs)—OH | 86.5 |
| Boc—Trp(Dmb)—OH | 60.7 |
| Boc—Trp(Tms)—OH | 83.7 |
| Boc—Trp(Mds)—OH | 80.2 |
| Boc—Trp(Mtr)—OH | 82.6 |

TEST EXAMPLE 2

Boc-Trp(Tms)-OH (0.1 mM) and Boc-Trp(Mtr)-OH (0.1 mM) were each treated with methanesulfonic acid (0.5 ml) in the presence of thioanisole (60 μl) and 1,2-ethanedithiol (60 μl) at room temperature for one hour. The reactant was diluted to 50 ml and subjected to amino acid analysis for estimating the yield of tryptophan. The results are set forth in Table 2.

TABLE 2

| Compound | Yield of Trp (%) |
| --- | --- |
| Boc—Trp(Tms)—OH | 34.8 |
| Boc—Trp(Mtr)—OH | 100 |

EXAMPLE 8

H-Trp(Mbs)-OH (375 mg, 1 mM) and triethylamine (0.12 ml, 1.5 mM) were dissolved in water (2 ml) followed by addition of a solution of 2-t-butyloxycarbonyl-4,6-dimethyl-2-mercaptopyrimidine (290 mg, 1.2 mM) in dioxane (2 ml). The mixture was stirred at room temperature for 15 hours, after which water (10 ml) and ether (5 ml) were added for extraction. The ether layer was extracted with a small amount of 5% aqueous sodium hydrogen carbonate. The water layers were combined and acidified with 10% aqueous citric acid. It was then extracted with ethyl acetate (20 ml) and the ethyl acetate layer was washed with water and dried over sodium sulfate. The solvent was distilled off and the residue was crystallized by addition of petroleum ether to give Boc-Trp(Mbs)-OH. Yield 452 mg (95.4%); m.p. 83°–84° C.; $[\alpha]_D^{23} -28.1°$ (c=0.5, DMF).

Elemental analysis: Calcd. for $C_{23}H_{26}N_2O_7S$: C, 58.21; H, 5.50; N, 5.90; S, 6.76; Found: C, 58.17; H, 5.85; N, 5.46; S, 6.81.

EXAMPLE 9

In acetonitrile (10 ml) were dissolved Boc-Trp(MBs)-OH (712 mg, 1.5 mM) and HONb (297 mg, 1.65 mM), and the solution was cooled to 0° C. To this solution was added DCC (340 mg, 1.65 mM) and the mixture was reacted at 0° C. for an hour and at room temperature for 15 hours. The precipitate was filtered off, and H-Gly-OBzl.p-toluenesulfonate (557 mg, 1.65 mM) and triethylamine (0.23 ml) were added to the filtrate. The reaction was conducted at room temperature for 5 hours, at the end of which time the solvent was distilled off. The residue was dissolved in ethyl acetate (20 ml), washed with 5% aqueous sodium hydrogen carbonate, 1 N-HCl and water in that order, and dried over anhydrous sodium sulfate. The solvent was distilled off and the residue was solidified with petroleum ether and recovered by filtration. The above procedure gave Boc-Trp(Mbs)-Gly-OBzl. Yield 850 mg (91.1%); m.p. 72°–74° C.; $[\alpha]_D^{24} -15.0°$ (c=0.5, DMF).

Elemental analysis: Calcd. for $C_{32}H_{35}N_3O_8S$: C, 61.82; H, 5.67; N, 6.76; S, 5.16; Found: C, 62.34; H, 5.74; N, 6.81 S, 4.60.

EXAMPLE 10

In trifluoroacetic acid (6 ml) was dissolved Boc-Trp(Mbs)-Gly-OBzl (622 mg, 1 mM) and the reaction was continued at room temperature for 20 minutes. The trifluoroacetic acid was distilled off, ether was added to the residue, and the resultant solid was recovered by filtration and dried. This trifluoroacetate was dissolved, together with Z-Gly-ONp (330 mg, 1 mM) and N-ethylmorpholine (0.13 ml), in acetonitrile (20 ml), and the solution was reacted at room temperature for 15 hours. The solvent was distilled off and the residue was dissolved in ethyl acetate (30 ml). The solution was washed with 1 N-aqueous ammonia, 1 N-HCl and water, and dried over anhydrous sodium sulfate. The solvent was distilled off, ether was added to the residue, and the resultant crystalline solid was recrystallized from ethyl acetate-ether to give Z-Gly-Trp(Mbs)-Gly-OBzl. Yield 580 mg (85.4%); m.p. 130°–131° C.; $[\alpha]_D^{24} -7.1°$ (c=0.5, DMF).

Elemental analysis: Calcd. for $C_{37}H_{36}N_4O_9S$: C, 62.34; H, 5.09; N, 7.86; S, 4.50; Found: C. 62.24; H, 5.02; N, 7.85; S, 4.78.

EXAMPLE 11

Z-Gly-Trp(Mbs)-Gly-OBzl (340 mg, 0.5 mM) was treated with hydrogen fluoride (5 ml) in the presence of ethane-dithiol (1.5 ml) and anisole (1.5 ml) at 0° C. for 2 hours. After the hydrogen fluoride was distilled off, water (10 ml) and ether (10 ml) were added and the insolubles were filtered off. The ether layer was discarded and the water layer was washed again with ether. The water layer was passed through a column of Amberlite IR-410 (acetate form, 1×10 cm) and the effluent and washings were combined and distilled. The residue was purified by partition chromatography (column: 4×45 cm; solvent:n-butanol-acetic acid-water=4:1:5). The fractions rich in the desired product were pooled and the solvent was distilled off. The residue was crystallized from ethanol and ether to give H-Gly-Trp-Gly-OH. Yield 98 mg (61.6%); m.p. 245°–246° C. (decomp.); $[\alpha]_D^{21} +3.76°$ (c=0.5, acetic acid).

Elemental analysis: Calcd. for C $C_{15}H_{18}O_4N_4.\frac{1}{2}H_2O.\frac{1}{2}CH_3COOH$: C, 53.77, H, 5.92 N, 15.68; Found: C, 53.48; H, 5.88; N, 15.15.

EXAMPLE 12

Boc-Trp(Tms)—OH (504 mg, 1 mM), H-Gly-OBzl.p-toluenesulfonate (371 mg, 1.2 mM), were dissolved, together with triethylamine (0.15 ml), in acetonitrile (10 ml). Then, DCC (227 mg, 1.1 mM) was added and the mixture was reacted at 0° C. for 2 hours and at room temperature for 15 hours. The precipitate was filtered off, after which the acetonitrile was distilled off. The residue was dissolved in ethyl acetate (20 ml) and washed with 5% aqueous sodium hydrogen carbonate, 1 N-HCl and water. After drying over anhydrous sodium sulfate, the ethyl acetate was distilled off to give Boc-Trp(Tms)-Gly-OBzl (453 mg, 67%) as an oil. This oil was treated with trifluoroacetic acid in the same manner as Example 10. The trifluoroacetate thus obtained was dissolved in acetonitrile (10 ml) followed by addition of Z-Lys(Z)-ONp (391 mg, 0.73 mM) and N-ethylmorpholine (0.1 ml). The reaction was conducted at room temperature for 48 hours, at the end of which time the solvent was distilled off. The residue was dissolved in ethyl acetate (30 ml), washed with 1 N-aqueous ammonia, 1 N-HCl and water in that order, and dried over anhydrous sodium sulfate. The ethyl acetate was distilled off and the residue was crystallized from ethyl acetate-ether and recovered by filtration to give Z-Lys(Z)-Trp(Tms)-Gly-OBzl. Yield 303 mg (48.4%); m.p. 98°–100° C.; $[\alpha]_D^{26} -12.9°$ (c=0.5, DMF).

Elemental analysis: Calcd. for $C_{51}H_{55}N_5O_{13}S$: C, 62.62; H, 5.67; N, 7.16; S, 3.28; Found: C, 62.67; H, 5.60; N, 7.24; S, 3.19.

EXAMPLE 13

Z-Lys(Z)-Trp(Tms)-Gly-OBzl (190 mg, 0.2 mM) was treated with hydrogen fluoride (5 ml) in the presence of ethanedithiol (0.8 ml) and anisole (0.8 ml) at 0° C. for one hour. The reaction mixture was worked up and purified with Sephadex G-25 in the same manner as Example 11. The fractions rich in the desired compound were pooled and the solvent was distilled off. The residue was lyophilized from water to give H-Lys-Trp-Gly-OH. Yield 80 mg (88.9%); $[\alpha]_D^{22} +31.4°$ (c=0.5, in 5% acetic acid). Amino acid analysis (hydrolysis with 6 N-HCl containing 4% of mercaptoethanol; the same applies below): Lys 1.00; Trp 0.84; Gly 1.03.

Elemental analysis: Calcd. for $C_{19}H_{27}N_5O_4 \cdot CH_3COOH \cdot 4H_2O$: C, 48.36; H, 7.54; N, 13.43; Found: C, 47.98; H, 7.23; N, 13.26.

EXAMPLE 14

Boc-Trp(Mds)-OH (251 mg, 0.5 mM), H-Gly-OBzl p-toluenesulfonate (186 mg, 0.55 mM) and HONb (114 mg, 0.6 mM) were dissolved in acetonitrile (5 ml), followed by addition of triethylamine (0.08 ml) and DCC (124 mg, 0.6 mM) at 0° C. The reaction mixture was worked up in the same manner as Example 12 to give Boc-Trp(Mds)-Gly-OBzl (300 mg, 96.9%) as an oil. As in Example 12, this product was further treated with trifluoroacetic acid and, then, reacted with Z-Lys(Z)-ONp (268 mg, 0.5 mM) in the presence of N-ethylmorpholine (0.07 ml). Finally, the reaction mixture was similarly worked up to give Z-Lys(Z)-Trp(Mds)-Gly-OBzl. Yield 132 mg (32%); m.p. 120° C.; $[\alpha]_D^{26} - 10.6°$ (c=0.5, DMF).

Elemental analysis: Calcd. for $C_{51}H_{55}N_5O_{11}S$: C, 64.74; H, 5.86; N, 7.40; S, 3.39; Found: C, 64.77; H, 5.80; N, 7.60; S, 3.30.

EXAMPLE 15

Z-Lys(Z)-Trp(Mds)-Gly-OBzl (76 mg, 0.08 mM) was treated with hydrogen fluoride (3 ml) in the presence of ethanedithiol (0.32 ml) and anisole (0.32 ml) at 0° C. for one hour. Thereafter, the reaction mixture was worked up and purified in the same manner as Example 13 to give H-Lys-Trp-Gly-OH. Yield 29 mg (80.5%); $[\alpha]_D^{22} + 28.9°$ (c=0.5, in 5% acetic acid). Amino acid analysis: Lys 1.00; Trp 0.82; Gly 1.01.

Elemental analysis: Calcd. for $C_{19}H_{27}N_5O_4 \cdot CH_3COOH \cdot 4H_2O$: C, 48.36; H, 7.54; N, 13.43; Found: C, 48.07; H, 7.33; N, 13.16.

EXAMPLE 16

In acetonitrile (10 ml) were dissolved Boc-Trp(Tms)-OH (2.94 g, 5.5 mM) and HONb (1.08 g, 6 mM), followed by addition of DCC (1.24 g, 6 mM) at 0° C. The reaction was conducted at 0° C. for one hour and, then, at room temperature for 15 hours to prepare a reactive ester. On the other hand, Boc-Ala-Val-Gly-OBzl (2.18 g, 5 mM) was dissolved in trifluoroacetic acid (15 ml) and reacted at room temperature for 20 minutes. The trifluoroacetic acid was distilled off and the residue was solidified with ether, recovered by filtration and dried. This solid product was dissolved in acetonitrile (20 ml) and neutralized with triethylamine (0.7 ml). To this neutralized solution was added the above reaction mixture containing said reactive ester after removal of insolubles therefrom by filtration, and the mixture was reacted at room temperature for 15 hours. This reaction mixture was extracted with water (100 ml) and ethyl acetate (150 ml). The organic layer was washed with 5% aqueous sodium hydrogen carbonate, 1 N-HCl and water in the order mentioned and dried over anhydrous sodium sulfate. The solvent was then distilled off and the residue was recrystallized from ethyl acetate-ether to give Boc-Trp(Tms)-Ala-Val-Gly-OBzl. Yield 3.50 g (82.2%); m.p. 115°–117° C.; $[\alpha]_D^{24} - 6.74°$ (c=0.5, DMF).

Elemental analysis: Calcd. for $C_{42}H_{53}N_5O_{12}S$: C, 59.21; H, 6.27; N, 8.22; S, 3.76; Found: C, 59.36; H, 6.45; N, 8.14; S, 3.70.

EXAMPLE 17

Boc-Trp(Tms)-Ala-Val-Gly-OBzl (3.40 g, 3.99 mM) was treated with trifluoroacetic acid in the same manner as Example 16. The resulting trifluoroacetate was dissolved in DMF (10 ml), followed by addition of triethylamine (0.66 ml) and Boc-Gln-ONb (1.79 g, 4.4 mM). The mixture was reacted at room temperature for 15 hours, after which it was extracted and purified as in Example 16. The product was then recrystallized twice from methanol-ether to give Boc-Gln-Trp(Tms)-Ala-Val-Gly-OBzl. Yield 2.60 g (66.4%); m.p. 210°–211° C.; $[\alpha]_D^{24} - 7.73°$ (c=0.5, DMF).

Elemental analysis: Calcd. for $C_{47}H_{61}N_7O_{14}S \cdot \frac{1}{2}H_2O$: C, 57.07; H, 6.32; N, 9.91; S, 3.24; Found: C, 57.08; H, 6.23; N, 9.98; H, 3.10.

EXAMPLE 18

Boc-Gln-Trp(Tms)-Ala-Val-Gly-OBzl (2.54 g, 2.59 mM) was treated with trifluoroacetic acid in the same manner as Example 16. The resulting trifluoroacetate was dissolved in DMF (10 ml) followed by addition of triethylamine (0.44 ml) and Boc-Asn-ONp (1.40 g, 3.12 mM). The mixture was reacted at room temperature for 48 hours. To the reaction mixture was added ether (50 ml) and the resulting precipitate was recovered by filtration. This precipitate was washed with hot acetonitrile to give Boc-Asn-Gln-Trp(Tms)-Ala-Val-Gly-OBzl. Yield 2.70 g (95.4%); m.p. 236° C. (decomp.); $[\alpha]_D^{24} - 25.4°$ (c=0.5, DMF).

Elemental analysis: Calcd. for $C_{51}H_{67}O_{16}N_9S$: C, 55.98; H, 6.17; N, 11.52; S, 2.93; Found: C, 55.86; H, 6.18; N, 11.55; S, 2.95.

EXAMPLE 19

Boc-Asn-Gln-Trp(Tms)-Ala-Val-Gly-OBzl (2.62 g, 2.39 mM) was dissolved in DMF (20 ml) and catalytic reduction was carried out using palladium black as the catalyst at room temperature for 4 hours. The catalyst was filtered off and the DMF was distilled off. The residue was crystallized by addition of ethyl acetate and filtered to give Boc-Asn-Gln-Trp(Tms)-Ala-Val-Gly-OH. Yield 2.39 g (99.6%); m.p. 220° C. (decomp.); $[\alpha]_D^{24} - 24.7°$ (c=0.5, DMF).

Elemental analysis: Calcd. for $C_{44}H_{61}N_9O_{16}S \cdot \frac{1}{2}H_2O$: C, 52.16; H, 6.17; N, 12.44; S, 3.17; Found: C, 52.24; H, 6.22; N, 12.54; S, 3.55.

EXAMPLE 20

In DMF (15 ml) were dissolved Boc-Asn-Gln-Trp(Tms)-Ala-Val-Gly-OH (2.01 g, 2 mM) and HONb (432 mg, 2.4 mM) followed by addition of DCC (618 mg, 3 mM) at 0° C. The mixture was reacted at 0° C. for 2 hours and at room temperature for 15 hours to prepare a reactive ester. On the other hand, Boc-His-Leu-Met-NH₂ (1.10 g, 2.2 mM) was treated with trifluoroacetic acid in the same manner as Example 16. This trifluoroacetate was dissolved in the filtrate containing said reactive ester. After addition of triethylamine (0.56 ml, 4 mM), the mixture was reacted at room temperature for 3 days. To this reaction mixture was added ether (50 ml) and the resulting precipitate was recovered by filtration and reprecipitated from 5% acetonitrile to give Boc-Asn-Gln-Trp(Tms)-Ala-Val-Gly-His-Leu-Met-NH₂. Yield 2.37 g (85.4%); m.p. 250° C. (decomp.); $[\alpha]_D^{24} - 18.1°$ (c=0.5, DMF).

Elemental analysis: Calcd. for $C_{61}H_{89}N_{15}O_{18}S_2 \cdot 2\text{-}H_2O$: C, 51.57; H, 6.60; N, 14.79; S, 4.51; Found: C, 51.54; H, 6.41; N, 14.27; S, 4.45.

EXAMPLE 21

Boc-Asn-Gln-Trp(Tms)-Ala-Val-Gly-His-Leu-Met-NH$_2$ (2.24 g, 1.62 mM) was treated with trifluoroacetic acid in the same manner as Example 16. The resulting trifluoroacetate was dissolved, together with Boc-Gly-ONb (653 mg, 1.94 mM), in DMF (15 ml), followed by addition of triethylamine (0.46 ml, 3.24 mM). The mixture was reacted at room temperature for 15 hours, at the end of which time acetonitrile was added. The resulting precipitate was recovered by filtration and reprecipitated from 85% acetonitrile to give Boc-Gly-Asn-Gln-Trp(Tms)-Ala-Val-Gly-His-Leu-Met-NH$_2$. Yield 1.92 g (82.2%); m.p. 251° C. (decomp.); $[\alpha]_D^{24} -17.3°$ (c=0.5, DMF).

Elemental analysis: Calcd. for $C_{63}H_{92}N_{16}O_{19}S_2 \cdot 3\text{-}H_2O$: C, 50.58; H, 6.60; N, 14.98; S, 4.29; Found: C, 50.61; H, 6.30; N, 14.67; S, 4.57.

EXAMPLE 22

Boc-Gly-Asn-Gln-Trp(Tms)-Ala-Val-Gly-His-Leu-Met-NH$_2$ (1.90 g, 1.32 mM) was treated with trifluoroacetic acid in the same manner as Example 16. The resulting trifluoroacetate was dissolved, together with Boc-Leu-ONp (558 mg, 1.58 mM), in DMF (10 ml), followed by addition of triethylamine (0.37 ml, 264 mM). The mixture was reacted at room temperature for 15 hours, after which it was worked up and purified as in Example 21 to give Boc-Leu-Gly-Asn-Gln-Trp(Tms)-Ala-Val-Gly-His-Leu-Met-NH$_2$. Yield 1.78 g (86.7%); m.p. 254° C. (decomp.); $[\alpha]_D^{24} -23.6°$ (c=0.5, DMF).

Elemental analysis: Calcd. for $C_{69}H_{103}N_{16}O_{19}S_2 \cdot 3\text{-}H_2O$: C, 51.50; H, 6.87; N, 14.80; S, 3.99; Found: C, 51.73; H, 6.64; N, 14.58; S, 4.08.

EXAMPLE 23

Boc-Leu-Gly-Asn-Gln-Trp(Tms)-Ala-Val-Gly-His-Leu-Met-NH$_2$ (1.09 g, 0.7 mM) was treated with trifluoroacetic acid (10 ml) at room temperature for 20 minutes. After addition of concentrated HCl, the trifluoroacetic acid was distilled off. To the residue was added ether and the precipitate was recovered by filtration and dried. This product was dissolved in DMF (5 ml) together with Aoc-Arg(Tos)-OH (372 mg, 0.84 mM), 1-hydroxybenzotriazole (123 mg, 0.91 mM) and triethylamine (0.2 ml). Then, 1-cyclohexyl-3-(2-morpholinoethyl)carbodiimide meso-p-toluenesulfonate (381 mg, 0.84 mM) was added at 0° C. The mixture was reacted at 0° C. for 2 hours and at room temperature for 48 hours. Thereafter, the reaction mixture was worked up and purified in the same manner as Example 22 to give Aoc-Arg(Tos)-Leu-Gly-Asn-Gln-Trp(Tms)-Ala-Val-Gly-His-Leu-Met-NH$_2$. Yield 942 mg (70.0%); m.p. 196°–199° C. (decomp.); $[\alpha]_D^{24} -18.5°$ (c=0.5, DMF).

Elemental analysis: Calcd. for $C_{83}H_{123}N_{21}O_{23}S_3 \cdot H_2O$: C, 52.53; H, 6.64; N, 15.50; S, 5.07; Found: C, 52.37; H, 6.69; N, 15.09; S, 5.37.

EXAMPLE 24

Aoc-Arg(Tos)-Leu-Gly-Asn-Gln-Trp(Tms)-Ala-Val-Gly-His-Leu-Met-NH$_2$ (920 mg, 0.49 mM) was treated with trifluoroacetic acid in the same manner as Example 16. The resulting trifluoroacetate was dissolved in DMF (10 ml) together with Boc-Gln-ONb (245 mg, 0.6 mM) and triethylamine (0.14 ml), and the solution was reacted at room temperature for 15 hours. The reaction mixture was then worked up and purified as in Example 21 to give Boc-Gln-Arg(Tos)-Leu-Gly-Asn-Gln-Trp(Tms)-Ala-Val-Gly-His-Leu-Met-NH$_2$. Yield 670 mg (68.6%); m.p. 245° C. (decomp.); $[\alpha]_D^{21} -24.1°$ (c=0.5, DMF).

Elemental analysis: Calcd. for $C_{87}H_{129}N_{23}O_{25}S_3 \cdot 2\text{-}H_2O$: C, 51.49; H, 6.51; N, 15.88; S, 4.74; Found: C, 51.45; H, 6.71; N, 15.84; S, 5.19.

EXAMPLE 25

Boc-Gln-Arg(Tos)-Leu-Gly-Asn-Gln-Trp(Tms)-Ala-Val-Gly-His-Leu-Met-NH$_2$ (650 mg, 0.326 mM) was treated with trifluoroacetic acid as in Example 16. The trifluoroacetate was dissolved in DMF (10 ml) together with z-pGlu-ONb (139 mg, 0.42 mM) and N-ethylmorpholine (0.083 ml), and the mixture was reacted at room temperature for 15 hours. The reaction mixture was then worked up and purified as in Example 21 to give Z-pGlu-Gln-Arg(Tos)-Leu-Gly-Asn-Gln-Trp(Tms)-Ala-Val-Gly-His-Leu-Met-NH$_2$. Yield 540 mg (77.5%), m.p. 247° C. (decomp.); $[\alpha]_D^{24} -27.0°$ (c=0.5, DMF).

Elemental analysis: Calcd. for $C_{95}H_{132}N_{24}O_{27}S_3 \cdot 4\text{-}H_2O$: C, 51.61; H, 6.38; N, 15.20; S, 4.35; Found: C, 51.40; H, 6.14; N, 15.26; S, 5.00.

EXAMPLE 26

Z-pGlu-Gln-Arg(Tos)-Leu-Gly-Asn-Gln-Trp(Tms)-Ala-Val-Gly-His-Leu-Met-NH$_2$ (150 mg, 0.07 mM) was treated with hydrogen fluoride (3 ml) in the presence of anisole (0.21 ml) and ethanedithiol (0.21 ml) at 0° C. for one hour. The hydrogen fluoride was distilled off, and water (20 ml) and ether (20 ml) were added to the residue. The insolubles were filtered off and, from the filtrate, the aqueous layer was taken and washed again with ether. The water layer was passed through a column of Amberlite IR-410 (acetate form, 1×10 cm) and the effluent and washings are combined and freeze-dried. The resulting crude product was purified by partition column chromatography on Sephadex G-25 (column:1.5×45 cm; solvent:n-butanol-acetic acid-water=4:1:5). The fractions rich in the desired compound were pooled and the solvent was distilled off. The residue was then lyophilized from water to give pGlu-Gln-Arg-Leu-Gly-Asn-Gln-Trp-Ala-Val-Gly-His-Leu-Met-NH$_2$ (bombesin). Yield 72 mg (63.5%); $[\alpha]_D^{22} -53.5°$ (c=0.5, in 5% acetic acid). Amino acid analysis: His 0.96; Arg 1.01; Trp 0.92; Asp 1.06; Glu 3.23; Gly 1.99; Ala 1.00; Val 0.93; Met 0.92; Leu 1.96.

Elemental analysis: Calcd. for $C_{71}H_{110}N_{24}O_{18}S_2 \cdot 2CH_3COOH \cdot 3H_2O$: C, 47.53; H, 6.97; N, 18.74; S, 1.79; Found: C, 47.65; H, 7.03; N, 18.46; S, 2.21.

EXAMPLE 27

In the same manner as Example 5, Boc-Trp-OBzl (1.97 g, 5 mM) was reacted with 4-methoxy-2,3,6-trimethylbenzene-sulfonyl chloride (1.87 g, 7.5 mM) in dichloromethane in the presence of sodium hydroxide (500 mg, 12.5 mM) and cetyltrimethylammonium chloride (16 mg, 0.05 mM). The reaction product was then hydrolyzed with an aqueous solution of sodium hydroxide to give Boc-Trp(Mtr)-OH. Yield 2.05 g (79.4%); m.p. 78°–80° C.; $[\alpha]_D^{22} -24.8°$ (c=0.5, DMF).

Elemental analysis: Calcd. for $C_{26}H_{32}N_2O_7S$: C, 60.44; H, 6.24; N, 5.42; S, 6.21; Found: C, 61.07; H, 6.25; N, 5.17 S, 5.83.

EXAMPLE 28

Z-Ser-Tyr-D-Leu-Leu-Arg(Mbs)-Pro-NH-C$_2$H$_5$ (315 mg, 0.292 mM) was reduced using palladium black as the catalyst in methanol at room temperature for 3 hours. The catalyst was filtered off and the solvent was distilled off. In acetonitrile were dissolved Boc-Trp(Mtr)-OH (187 mg, 0.35 mM) and HONb (69 mg, 0.38 mM), followed by addition of DCC (83 mg, 0.4 mM) at 0° C. The mixture was reacted at 0° C. for 30 min. and at room temperature for 4 hours. After the precipitate was filtered off, to the resulting filtrate was added the solution containing said amine component in DMF (5 ml), and the mixture was reacted at room temperature for 15 hours. The solvent was distilled off and the residue was treated with ether to give Boc-Trp(Mtr)-Ser-Tyr-D-Leu-Leu-Arg(Mbs)-Pro-NH-C$_2$H$_5$ as a powder product. The resulting product was recrystallized from methanol-ether. Yield 297 mg (70.0%); m.p. 151°–152° C.; $[\alpha]_D^{22} -32.4°$ (c=0.5, DMF).

Elemental analysis: Calcd. for C$_{69}$H$_{96}$N$_{12}$O$_{19}$S$_2$.2H$_2$O: C, 56.81; H, 6.94; N, 11.35; S, 4.33; Found: C, 56.87; H, 6.95; N, 11.60; S, 3.91.

EXAMPLE 29

Boc-Trp(Mtr)-Ser-Tyr-D-Leu-Leu-Arg(Mbs)-Pro-NH-C$_2$H$_5$ (280 mg, 0.194 mM) was treated with trifluoroacetic acid (2 ml) at room temperature for 30 min, followed by addition 7 N-HCl/dioxane (0.1 ml). The mixture was treated with ether and the resulting precipitate was recovered by filtration as powder. The thus obtained hydrochloride, together with Z-pGlu-His-OH (96 mg, 0.24 mM) and HONb (53 mg, 0.3 mM), was dissolved in DMF (2 ml) and then the mixture was neutralized with N-ethylmorpholine (24 μl).

After addition of DCC (49 mg, 0.24 mM) at 0° C., the reaction was carried out at 0° C. for 2 hours and at room temperature for 48 hours and then the mixture was filtered, followed by evaporation of the solvent. The residue was reprecipitated from methanol-ether to give Z-pGlu-His-Trp(Mtr)-Ser-Tyr-D-Leu-Leu-Arg(Mbs)-Pro-NH-C$_2$H$_5$ (319 mg, 84%). The protected peptide (180 mg, 0.092 mM) was treated with methanesulfonic acid (1.5 ml) in the presence of ethanedithiol (0.1 ml, 1 mM) and thioanisole (0.15 ml, 1.5 mM) at room temperature for one hour.

To the reaction product ether was added, and the obtained oily product, after washing, was dissolved in a small amount of water. The solution was passed through a column (0.5×10 cm) of Amberlite IRA-410 (acetate form). The effluent, together with washings, was passed through a column (1.5×30 cm) of CM-cellulose, and then eluted by the linear gradient method using buffer solution of ammonium acetate (pH 6.8, 0.005–0.15 M, 300 ml each). The fractions rich in the desired compound were pooled and then poured into a column (1.2×7 cm) of Amberlite XAD-2. The elution was carried out by the linear gradient method using aqueous ethanol (5 to 80%, 200 to 200 ml each). The fractions containing pure desired product were pooled and ethanol was distilled off. The residue was then lyophilized from water. The obtained powder was dissolved in a small amount of 0.1 M-acetic acid-ethanol (2:3), and then the solution was poured into a column (1.5×45 cm) of Sephadex LH-20 and eluted using the same solvent. The fractions containing pure objective compound were pooled and lyophilized to give pGlu-His-Trp-Ser-Tyr-D-Leu-Leu-Arg-Pro-NH-C$_2$H$_5$. Yield 43 mg (38.6%); $[\alpha]_D^{26} -33.0°$ (c=0.5, in 5% acetic acid). Amino acid analysis: His 0.92; Arg 1.00; Trp 0.88; Ser 0.91; Glu 1.02; Pro 1.06; Leu 2.03; Tyr 1.09.

Elemental analysis: Calcd. for C$_{59}$H$_{84}$N$_{16}$O$_{12}$.CH$_3$COOH.6H$_2$O: C, 53.18; H, 7.31; N, 16.27; Found: C, 53.18; H, 6.99; N, 16.94.

EXAMPLE 30

Boc-Gln-resin (2.5 g, Gln content; 1.35 mM), which was synthesized by introduction of Boc-Gln-OH to chloromethylated polystyrene (divinylbenzene 2%, 200–400 mesh, Cl content; 0.6 mM/g), was put into a vessel for solid-phase peptide synthesis. Boc-Asn-OH, Boc-Asp(OBzl)-OH, Boc-Trp(Tms)-OH, Boc-Lys(Pms)-OH, Boc-Leu-OH, Boc-Pro-OH, Boc-Arg(Tos)-OH, Boc-Ile-OH, Boc-Phe-OH, Boc-Gly-OH and Boc-Tyr(Bzl)-OH were introduced into said resin by the following cycle.

Dichloromethane (1.5 min×3 times)→50% trifluoroacetic acid/dichloromethane (1.5 min. and 20 min.)→dichloromethane (1.5 min×2 times)→25% dioxane/dichloromethane (1.5 min.×2 times)→10% triethylamine/dichloromethane (1.5 min. and 10 min.)→dichloromethane (1.5 min.×4 times)→symmetric Boc-amino acid anhydride (5.4 mM) newly synthesised by the conventional manner using Boc-amino acid and DCC [after the reaction for 20 min., N-ethylmorpholine (87 μl) was added and further the reaction was carried out for 20 min.]→dichloromethane (1.5 min.)→symmetric Boc-amino acid anhydride and N-ethylmorpholine were reacted by the method above-mentioned→dichloromethane (1.5 min.×2 times)→33% ethanol/dichloromethane. Amino acid residues were successively introduced into said resin by the above cycle to give Boc-Tyr(BZl)-Gly-Gly-Phe-Leu-Arg(Tos)-Arg(Tos)-Ile-Arg(Tos)-Pro-Lys(Pms)-Leu-Lys(Pms)-Trp(Tms)-Asp(OBzl)-Asn-Gln-resin (3.83 g).

1.5 g of said protected peptide-resin was treated with hydrogen fluoride (20 ml) in the presence of anisol (3 ml) and 1,2-ethanedithiol (2 ml) at 0° C. for one hour. Hydrogen fluoride was distilled off, and ethyl acetate (15 ml) and water (20 ml) were added to the residue and after stirring, the resin was filtered off. The water layer of the filtrate was taken, further rinsed with ethyl acetate. The water layer was passed through a column (2×20 cm) of Amberlite IRA-410 (acetate form), and the effluent, together with washings, was lyophilized. The obtained powder was dissolved in a small amount of water, and the solution was poured into a column (2.5×6 cm) of CM-cellulose. The elution was carried out by the linear gradient method using buffer solution of ammonium acetate (pH 6.8, 0.005–0.6 M in water, 400 ml–400 ml). The fractions containing the desired compound were pooled, and then the lyophilization was carried out repeatedly. Dried powder was subjected to purification using preparative high performance liquid chromatography (Toyo Soda, Japan, LS-410, 2.14×37.5 cm). After elution with the solvent (acetonitrile:water=23:77, containing 0.1% trifluoroacetic acid), the fractions which contained the desired product were pooled. Acetonitrile only was distilled off, and then the residual aqueous solution was passed through a column (2×5 cm) of Amberlite IRA-410 (acetate form). The effluent, together with washings, was lyophilized. The obtained powder was dissolved in a small amount of 1 M-acetic acid and the solution was poured into a column (1.8×90 cm) of Sephadex G-25, which was developed by said acetic acid solution. The fractions which contained the objective compound were pooled, and lyophilized to give dynorphin (H-Tyr-Gly-Gly-Phe-Leu-Arg-Arg-Ile-Arg-Pro-Lys-Leu-Lys-Trp-Asp-Gln.OH). Yield 12 mg; $[\alpha]_D^{24} -58.4°$ (c=0.3, in 1% acetic acid). Thin-layer chromatography, Rf (avicel, developing solvent; butanol:pyridine:acetic acid:water=30:20:6:24)=0.64. Amino acid analysis: Lys 1.95; Arg 2.86; Trp 0.98; Asp 2.07; Glu 1.07; Pro 1.15; Gly 2.02; Ile 0.87; Leu 1.97; Tyr 1.00; Phe 0.98 (recovery 67%).

EXAMPLE 31

In the same manner as Example 5, Z-Trp-OBZl (15.0 g, 35 mM) and 4-methoxy-2,3,6-trimethylbenzenesulfonyl chloride were reacted in dichloromethane (500 ml) in the presence of sodium hydroxide (17.8 g, 0.44 M). The reaction product was then hydrolyzed with an aqueous solution of sodium hydroxide to give Z-Trp(Mtr)-OH. Yield 19.0 g (98.4%); m.p. 71°–74° C.; $[\alpha]_D^{24} -41.6°$ (c=0.9, DMF).

Elemental analysis: Calcd. for $C_{29}H_{31}O_7N_2S$: C, 63.14; H, 5.67; N, 5.08 S, 5.81; Found: C, 63.44; H, 5.89; N, 4.66 S, 5.62.

What we claim is:

1. A compound of the formula:

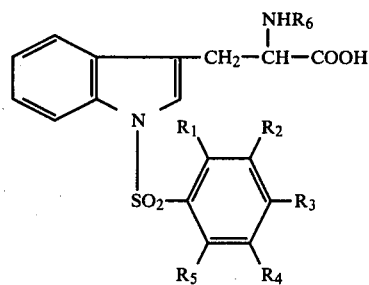

wherein $R_1$ and $R_5$ each is hydrogen, methyl or methoxy; $R_2$ and $R_4$ each is hydrogen or methyl; $R_3$ is methyl or methoxy; and $R_6$ is hydrogen or an α-amino-protecting group.

2. The compound as claimed in claim 1, wherein $R_1$, $R_2$, $R_4$ and $R_5$ are hydrogen, and $R_3$ is methyl.

3. The compound as claimed in claim 1, wherein $R_1$ to $R_5$ are methyl.

4. The compound as claimed in claim 1, wherein $R_1$, $R_3$ and $R_5$ are methoxy, and $R_2$ and $R_4$ are hydrogen.

5. The compound as claimed in claim 1, wherein $R_1$ and $R_3$ are methoxy and $R_2$, $R_4$ and $R_5$ are hydrogen.

6. The compound as claimed in claim 1, wherein $R_1$, $R_2$, $R_4$ and $R_5$ are hydrogen and $R_3$ is methoxy.

7. The compound as claimed in claim 1, wherein $R_1$ and $R_5$ are methyl, $R_2$ and $R_4$ are hydrogen and $R_3$ is methoxy.

8. The compound as claimed in claim 1, wherein $R_1$, $R_2$ and $R_5$ are methyl, $R_3$ is methoxy and $R_4$ is hydrogen.

9. The compound as claimed in claim 1, wherein $R_1$, $R_2$, $R_4$ and $R_5$ are methyl and $R_3$ is methoxy.

* * * * *